United States Patent
Soccol et al.

(10) Patent No.: US 9,683,968 B2
(45) Date of Patent: Jun. 20, 2017

(54) COMBINATION SENSOR

(71) Applicant: NXP B.V., Eindhoven (NL)

(72) Inventors: Dimitri Soccol, Rotselaar (BE);
Annelies Falepin, Hoegaarden (BE)

(73) Assignee: NXP B.V., Eindhoven (NL)

( * ) Notice: Subject to any disclaimer, the term of this patent is extended or adjusted under 35 U.S.C. 154(b) by 322 days.

(21) Appl. No.: 14/306,919

(22) Filed: Jun. 17, 2014

(65) Prior Publication Data

US 2015/0362393 A1    Dec. 17, 2015

(51) Int. Cl.
| | |
|---|---|
| *G01N 29/02* | (2006.01) |
| *G01N 29/036* | (2006.01) |
| *G01N 33/00* | (2006.01) |
| *G01N 29/04* | (2006.01) |
| *G01N 29/24* | (2006.01) |
| *G01N 29/28* | (2006.01) |

(52) U.S. Cl.
CPC ......... *G01N 29/036* (2013.01); *G01N 29/043* (2013.01); *G01N 29/2468* (2013.01); *G01N 29/28* (2013.01); *G01N 33/004* (2013.01); *G01N 2291/014* (2013.01); *G01N 2291/021* (2013.01); *G01N 2291/0231* (2013.01); *G01N 2291/0235* (2013.01); *G01N 2291/044* (2013.01)

(58) Field of Classification Search
CPC ..... G01N 29/036; G01N 29/12; G01N 33/004
USPC .............. 73/23.35, 23.4, 24.01, 24.06, 31.04
See application file for complete search history.

(56) References Cited

U.S. PATENT DOCUMENTS

| | | | |
|---|---|---|---|
| 4,361,026 A * | 11/1982 | Muller | G01N 29/022 |
| | | | 331/107 A |
| 7,146,857 B2 | 12/2006 | Hök | |
| 2005/0109080 A1* | 5/2005 | Hok | G01N 29/036 |
| | | | 73/24.01 |
| 2005/0262943 A1 | 12/2005 | Claydon et al. | |

FOREIGN PATENT DOCUMENTS

| | | |
|---|---|---|
| EP | 1 325 319 B1 | 6/2008 |
| EP | 2492240 A1 | 8/2012 |
| WO | 93/07463 | 4/1993 |

OTHER PUBLICATIONS

Extended European Search Report for application No. 15172516.5 (Oct. 21, 2015).
Benedetto, G., et al; "Precision measurement of speed of sound in gases"; Proceedings of the 16th IEEE Instrumentation and Measurement Technology Conference, vol. 22, N. 6; 42 pages (1991).

(Continued)

*Primary Examiner* — Benjamin Schmitt (57) ABSTRACT

One example discloses a combination sensor, comprising: a pressure sensor having an actuator which has a first resonant frequency; a cavity, coupled to the pressure sensor and able to receive a substance; wherein the cavity, in an absence of the substance, has a second resonant frequency in response to excitation by the actuator; wherein the cavity, in a presence of the substance, has a third resonant frequency in response to excitation by the actuator; wherein the first resonant frequency differs from the second and third resonant frequencies; and a sensor circuit which outputs a substance detected signal in response to the third resonant frequency in the cavity.

19 Claims, 8 Drawing Sheets

(56) References Cited

OTHER PUBLICATIONS

Granstedt, F., et al; "Gas Sensor with Electroacoustically Coupled Resonator"; Sensors and Actuators B—Chemical, No. 78, No. 1-3; pp. 161-165 (2001).
Granstedt, F., et al; "New $CO_2$ sensor with high resolution and fast response"; Proceedings of the $23^{rd}$ Annual International Conference of the IEEE Engineering in Medicine and Biology Society, No. 3, pp. 3100-3103 (2001).
Phillips, S., et al; "Theory for a gas composition sensor based on acoustic properties"; Institute of Physics Publishing Measurement Science and Technology, No. 14; pp. 70-75 (2003).

\* cited by examiner

500

Table 1

| Resonant Frequency | Substance |
|---|---|
| F1 | Actuator resonant frequency |
| F2 | Cavity resonance with calibration substance |
| F3-F4 | Carbon Dioxide (CO2) at various concentrations |
| F5-F6 | Mixtures of Nitrogen and Argon |
| F7-F8 | Target Gas |
| F9-F10 | Target Liquid |
| F11-F12 | Target Solid |
| F13-F14 | Target Chemical |
| F15-F16 | Target Molecule |
| F17-F18 | Target Pathogen |

COMBINATION SENSOR

BACKGROUND

Brief Background Introduction

This specification relates generally to articles and devices for sensing, and in one example to a combination sensing article or device.

SUMMARY

A combination sensor, comprising: a pressure sensor having an actuator which has a first resonant frequency; a cavity, coupled to the pressure sensor and able to receive a substance; wherein the cavity, in an absence of the substance, has a second resonant frequency in response to excitation by the actuator; wherein the cavity, in a presence of the substance, has a third resonant frequency in response to excitation by the actuator; wherein the first resonant frequency differs from the second and third resonant frequencies; and a sensor circuit which outputs a substance detected signal in response to the third resonant frequency in the cavity.

An article of manufacture comprising at least one non-transitory, tangible machine readable storage medium containing executable machine instructions for operating a combination sensor, the instructions comprising: exciting an actuator in a pressure sensor coupled to a cavity over a range of frequencies; monitoring a power level required to excite the actuator; comparing the actuator power level, at a predetermined frequency dependent upon the cavity dimensions, to a threshold power level; and outputting a substance detected signal if the monitored actuator power level at the predetermined frequency is below the threshold power level.

The above summary is not intended to represent every example embodiment within the scope of the current or future Claim sets. Additional example embodiments are discussed within the Figures and Detailed Description below.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

A sensor based on a measurement of the velocity of sound depends upon the substance (e.g. medium, gas, liquid, solid, plasma, etc.) through which the sound wave propagates.

If the substance is a gas, the classical ideal gas equation is often used (see Equation 1, where c is the sound velocity [m/s], R=8.314 J/mol K is the universal gas constant, T is the absolute temperature [K], $\gamma$ is the ratio between the heat capacities at constant pressure and constant volume, and $M_w$ the molecular mass [kg/mol] of the gas).

$$c = \sqrt{\frac{RT\gamma}{M_w}} \qquad \text{Equation 1}$$

However for other substances, a more general equation for the speed of sound in a medium is used (see Equation 2, where K is the bulk modulus of the medium [kg/(m²s²)], $\rho$ is the medium's density [kg/m³]).

$$c = \sqrt{\frac{K}{\rho}} \qquad \text{Equation 2}$$

In the case of a gas, Equation 1 shows that the ambient temperature has a direct influence on the speed of sound, however gas pressure does not.

When looking at a gas mixture (such as air), the ideal gas law predicts that the Molecular weight $M_w$ and the heat capacity ratio $\gamma$ will be average weighted by a partial pressure of the respective components. Consequently when the gas composition changes, both factors $\gamma$ and $M_w$ will change.

The values of $M_w$, $\gamma$ and $\gamma/M_w$ for the main gas components in air are shown in the following table.

|  | Gas | | | | |
| --- | --- | --- | --- | --- | --- |
|  | $N_2$ | $O_2$ | $H_2O$ | Ar | $CO_2$ |
| $M_w$ [g/mole] | 28.01 | 32.00 | 18.02 | 39.95 | 44.01 |
| $\gamma$ | 1.404 | 1.4 | 1.33 | 1.67 | 1.3 |
| $\gamma/M_w$ [mole/kg] | 49.98 | 43.75 | 73.83 | 41.55 | 29.08 |

This Table shows that an increase in relative humidity ($H_2O$) will increase the speed of sound, while an increase in $CO_2$ concentration decreases the speed of sound. Changes in the amount of $N_2$, $O_2$ or Ar will have only a limited influence.

Figure 1A:
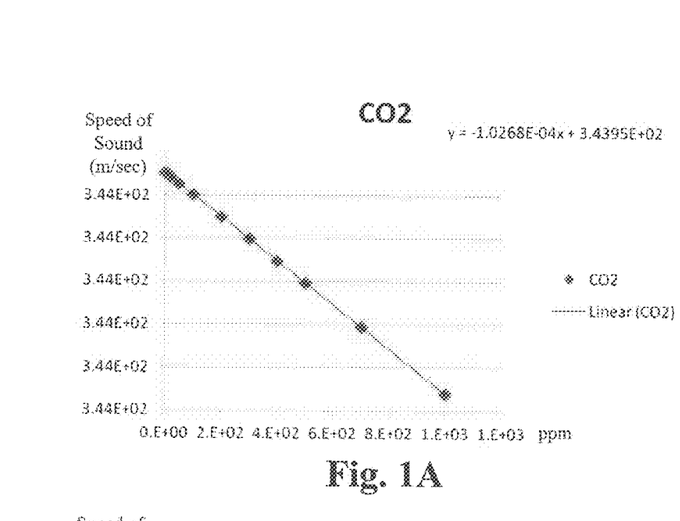
FIGS. 1A, 1B, 1C, 1D and 1E show a dependence of speed of sound on various parameters.
Figure 1B:
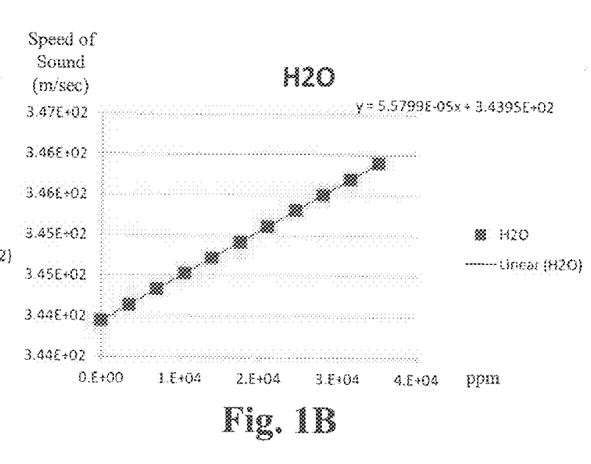
Figure 1C:
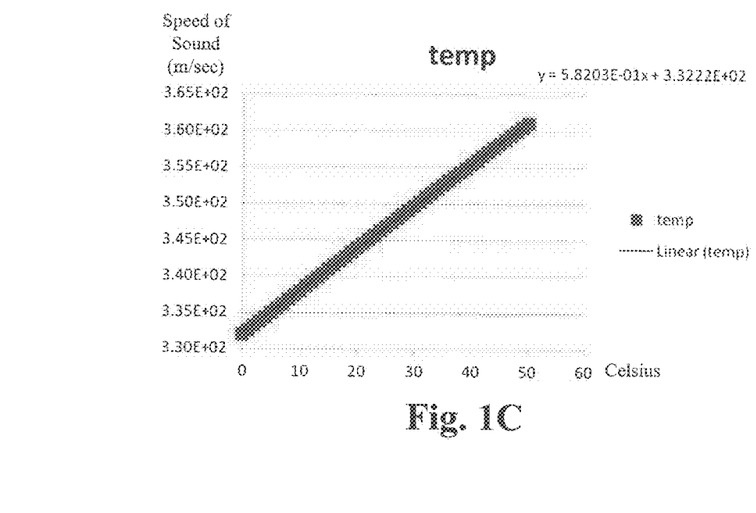
Figure 1D:
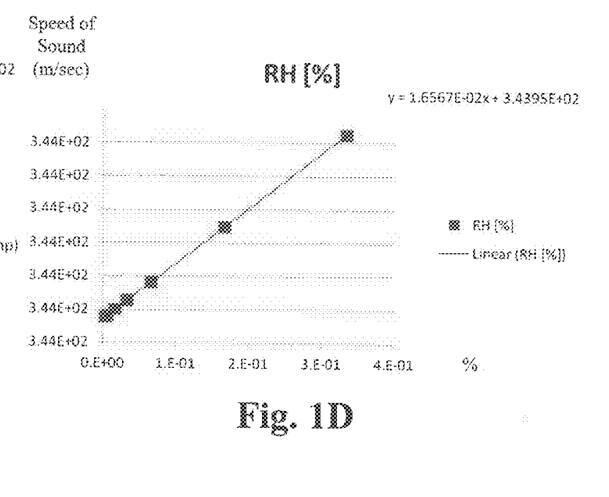
Figure 1E:
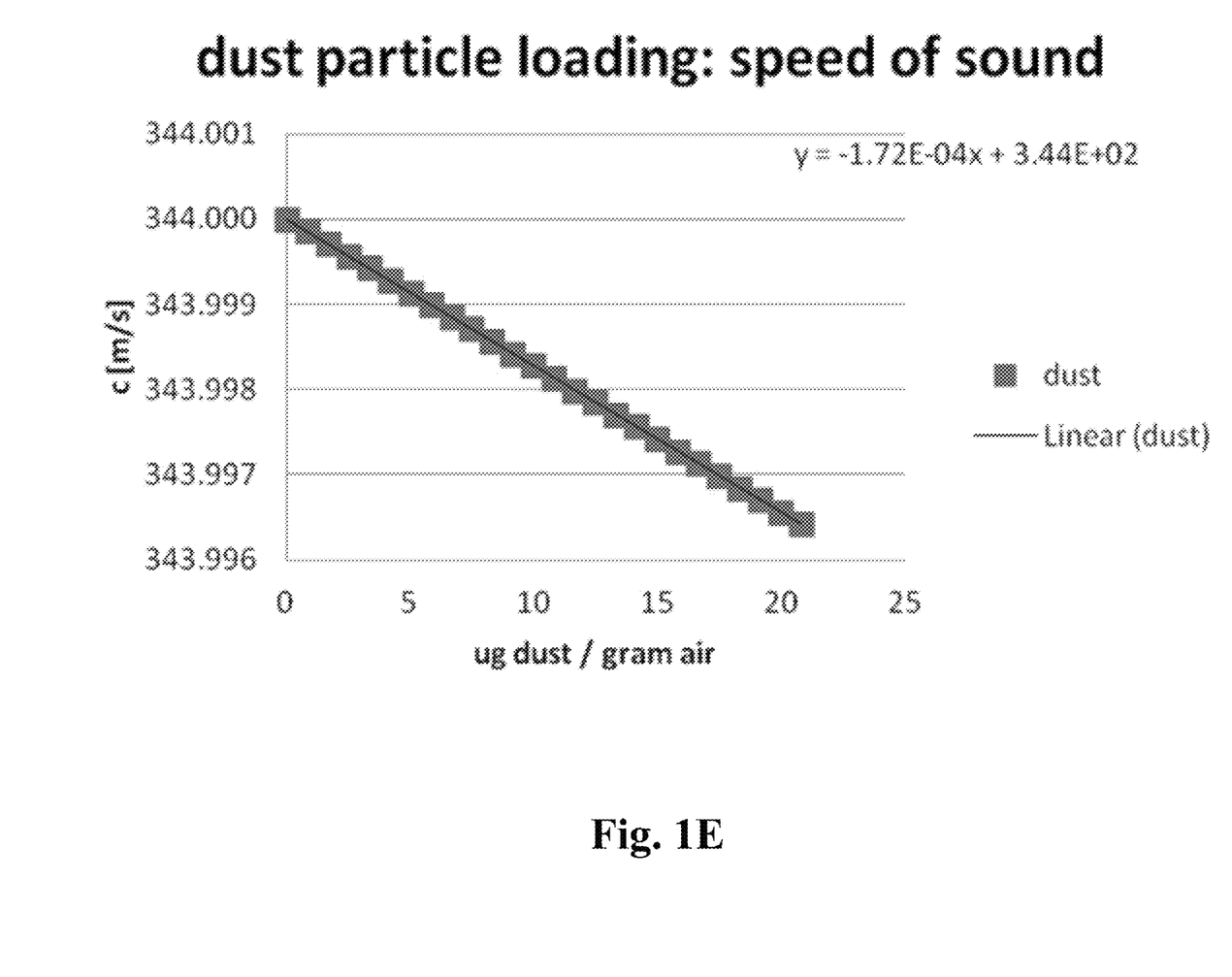

FIGS. 1A, 1B, 1C, 1D and 1E present graphs showing a calculated dependence of the speed of sound (meters/sec) based on various parameters. FIG. 1A shows theoretical speed of sound dependence on ppm of carbon-dioxide gas (CO2). FIG. 1B shows theoretical speed of sound dependence on ppm of pure water (H2O). FIG. 1C shows theoretical speed of sound dependence on temperature of 1.69 $10^3$ ppm change in c per degree Celsius. FIG. 1D shows theoretical speed of sound dependence on relative humidity in %. FIG. 1E shows theoretical speed of sound dependence on μgrams of dust per gram of air. Dust has a similar effect on the speed of sound as increasing $CO_2$ concentrations, namely the speed of sound decreases with increasing concentrations. When comparing the sensitivity numbers from the "dust" graph to the $CO_2$ sensitivity, +20 micrograms/m³ fine dust has the same effect as +33.5 ppm $CO_2$.

Although Equation 1 shows that the relation between c and the ratio $\gamma/M_w$ is non-linear, a good linear fit for small compositional changes (up to 3% for $H_2O$ sensitivity) is possible. A theoretical sensitivity of −0.30 ppm change per ppm $CO_2$ and +0.16 ppm change per ppm $H_2O$ is also possible. Expressed in % RH, the sensitivity will be +48 ppm per % RH. For instance, for a $CO_2$ sensor, a RH resolution of 1.25% RH is required in order to resolve steps of 200 ppm $CO_2$.

The relation between the speed of sound, a resonance frequency, and wavelength is defined in Equation 3 as:

$$c_{air} = f\lambda \quad \text{Equation 3}$$

In view of the information just presented, a speed of sound sensor can be created using a resonant cavity. A sound wave actuated into the cavity creates an acoustic resonance at a frequency determined by the dimensions (width, height, length) of the cavity and the speed of sound for a substance in the cavity.

In an idealized case, resonance appears in an open cavity for $d = n \cdot \lambda/2$ while at $d = (2 \cdot n - 1) \cdot \lambda/4$ for a closed cavity (where n is an integer number and d is a dimensional parameter along the propagation direction of the sound wave. It can be a length, width or height. The target of the cavity is to create a standing wave. The position of the normal modes of the standing waves depend on the "boundary conditions" in the resonator cavity (open vs. closed cavity). The included formula can be used to calculate the dimensions which are required to create a standing wave for a known excitation frequency (i.e. calculate the lowest possible frequency for a fixed dimension). For n=1, the fundamental mode will be found, namely the combined lowest frequency—smallest dimension optimum.

A combination sensor which both measures pressure and the speed of sound to determine the composition of a gas is now discussed. The phrase "combination sensor" is herein defined to be a device performing two or more sensing functions (for example: pressure sensing and substance detection). The sensor is based on actively actuating the pressure sensor combined with an acoustic resonance cavity. This sensor offers the advantage of a physical measurement principle, with similar sensitivity as the heated wire—thermal conductivity sensor, but without pressure cross-sensitivity.

Example embodiments of the combination sensor combine passive (capacitive) and active (Q-factor and resonance) measurements, allowing for the transduction of both pressure and gas composition (via speed of sound) with only 1 transducer. If a temperature sensor is not included with an embodiment of the combination sensor, temperature differences can be calibrated out by performing differential measurements on two MEMS actuators with an open and closed cavity.

In one example, the combination sensor is a modified pressure sensor with a connecting cavity which is tuned to be an acoustic sensor for identifying a composition of binary or other gases and for identifying other substances.

The combination sensor can be produced by a CMOS compatible flow by adding a few steps to a pressure sensor design or packaging flow. The sensor is functional at a broad temperature range thanks to its physical transduction mechanism, after temperature calibration and correction.

In other example embodiments the combination sensor is embedded in at least one from a group consisting of: a CO2 monitoring system, an indoor monitoring system, a food quality monitoring system, an air quality control system, humidity control system, and a mobile device. In another example embodiment, the combination sensor is a combination gas pressure sensor and carbon dioxide level sensor, and the cavity 206 has a predetermined resonant frequency in response to excitation by the membrane when carbon dioxide is in the cavity.

Figure 2:
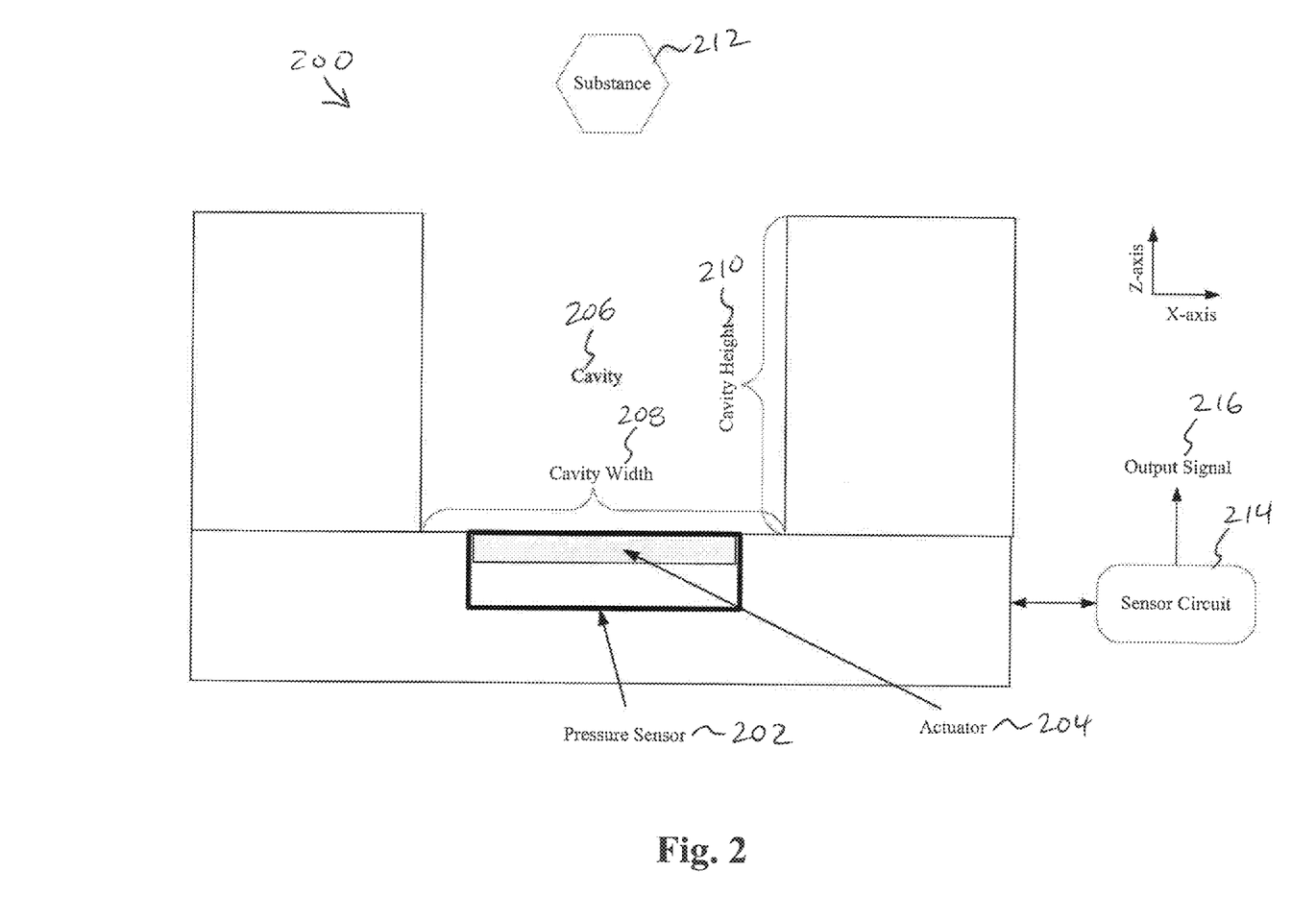
FIG. 2 is one example of a side view of a first combination sensor.
Figure 3:
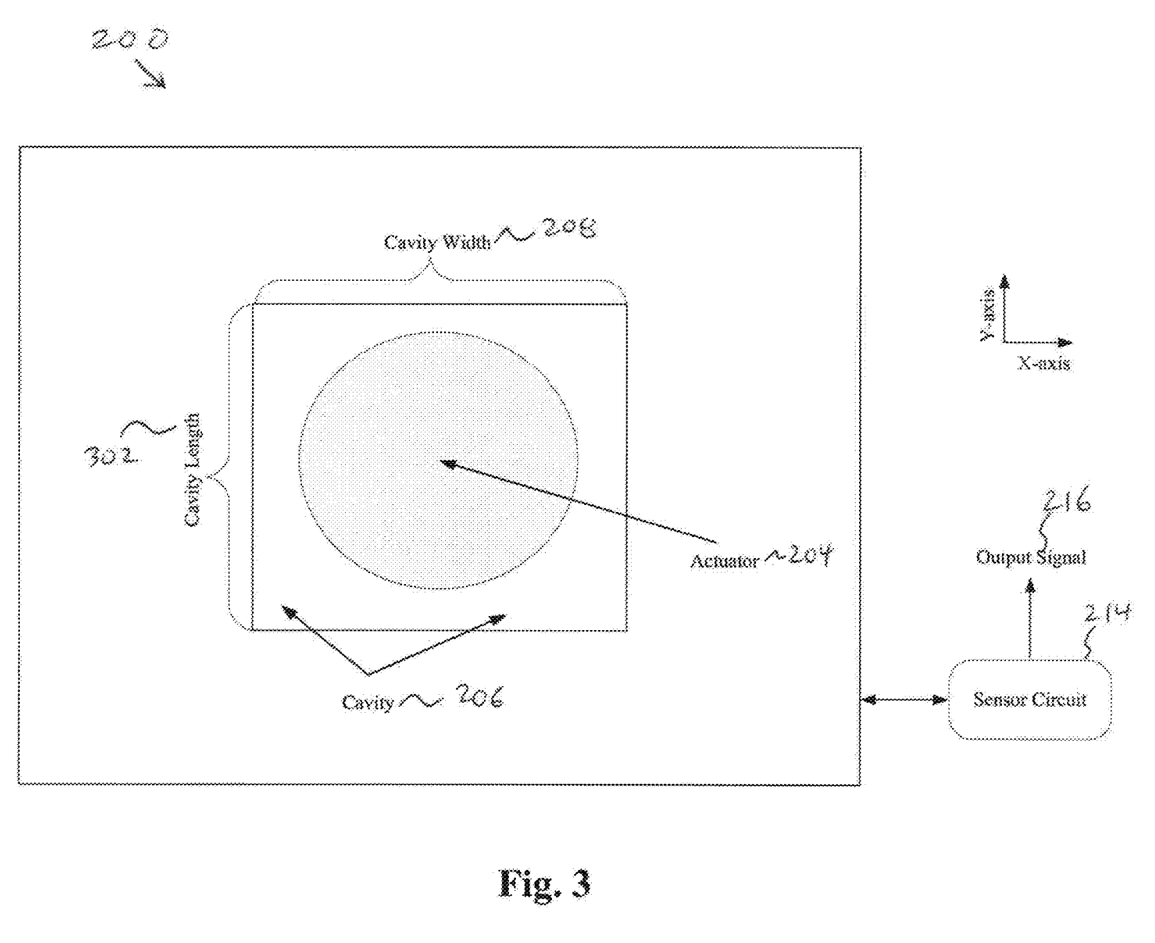
FIG. 3 is one example of a top view of the first combination sensor.

FIG. 2 is one example of a side view of a first combination sensor 200, and FIG. 3 is one example of a top view of the first combination sensor 200. FIGS. 2 and 3 are discussed together. The combination sensor 200, includes: a pressure sensor 202 having an actuator 204 which has a first resonant frequency; a cavity 206, coupled to the pressure sensor 202 and able to receive a substance 212. In one example embodiment the actuator 204 is a capacitive pressure sensor membrane 204.

The cavity 206 has physical dimensions including a width 208, a height 210 and a length 302 (see FIG. 3). The cavity 206 dimensions 208, 210 and 302 are tuned for a set of desired resonant frequencies during fabrication of the cavity 206. Excitation of the actuator 204 generate a wave pattern in the cavity 206 which may or may not be a resonant frequency depending upon a presence of a target substance 212. The actuator 204 is used to both drive vibrations in the cavity 206 and read-out resonant vibrations.

In one example the cavity 206, in an absence of the substance 212, has a second resonant frequency in response to excitation by the actuator 204; and in a presence of the substance 212, has a third resonant frequency in response to excitation by the actuator 204. A sensor circuit 214 (discussed further below) outputs a substance 212 detected signal 216 in response to the third resonant frequency in the cavity 206.

The second resonant frequency depends upon a speed of sound in the "empty" cavity 206, and the third resonant frequency depends upon a speed of sound when the substance 212 is in the cavity 206.

To enhance a substance detection sensitivity, the first resonant frequency of the actuator 204 is designed to differ from the second and third resonant frequencies, which indicate whether a substance 212 is present in the cavity 206 or not. Thus the resonant cavity 206 and the pressure sensor membrane 204 can be designed to have their own resonant frequencies.

The resonant frequency (e.g. Eigen-frequency) of the actuator 204 depends upon stiffness and dimensions of the actuator 204. With a cavity 206 of a specific size next to the actuator 204, a frequency at which the cavity 206 will resonate can be chosen.

A cavity 206 of one size will amplify the resonant frequency of the actuator 204, while a cavity 206 of a different size will resonate when a target substance is present in the cavity 206. Thus designing the cavity 206 resonance frequency to be strongly different from the MEMS actuator's 204 (e.g. pressure sensor membrane's) resonant frequency (e.g. Eigen-frequency) enables the cavity 206 resonance to be better distinguished from the pressure sensor membrane 204 resonance. The greater a difference between the acoustic cavity 206 resonance frequency and the MEMS actuator 204 resonance frequency, then the better resonance of the acoustic cavity 206 can be distinguished from pressure sensor membrane 204 resonance, thereby resulting in more sensitive detection to the target substance 212 in the acoustic cavity 206.

Another way to increase sensitivity is to design the first resonant frequency (i.e. the actuator's 204 resonant frequency) to be higher than the second and third resonant frequencies.

In one example, the combination sensor 200 is designed to sense pressure and detected CO2 gas. A corresponding cavity 206 can be an open cavity formed during a molding process and having a resonance frequency in the order of 10 kHz. Such a combination sensor 200 can be formed using a pressure sensor 202 with a circular diameter~50 µm pressure sensor membrane 204 (see FIG. 3). The membrane's 204 resonant frequency would then be in the order of magnitude of 1-10 MHz. Thus, a membrane 204 driving frequency for detecting resonance in the cavity 206 would be around 10 to 100 kHz and the cavity's 206 dimensions would be in the range of few millimeters. With this design the combination sensor 200 maintains a similar theoretical level of sensitivity to $CO_2$ in air (and similar cross-sensitivities to T and $H_2O$), but is insensitive to pressure differences.

In one example the combination sensor 200 is formed at least in part from at least one from a group consisting of: bulk wafer material, wafer surface material deposition, overmolding, packaging, a MEMS device and a CMOS device. Because of CMOS compatibility, the combination sensor 200 can be integrated on top of CMOS electronics.

In one example the sensor circuit 214 includes a driver module, an actuator power level monitor and a detection module. Power from the driver module excites the actuator 204, thereby creating a pressure wave in the cavity 206.

The driver module in one example includes a frequency generator. The frequency generator excites the actuator 204 over a range of frequencies. The sensor circuit 214 excites the actuator 204 over a range of frequencies so as to profile the cavity 206 and scan for substances 212.

In certain embodiments where the actuator 204 is also the pressure sensor's 202 membrane, the frequency generator does not excite the actuator 204 while the sensor circuit 214 is using the pressure sensor 202 to monitor a pressure in the cavity 206, since same pressure sensor membrane is used for both functions.

The detection module includes a first threshold power level and outputs the substance 212 detected signal if a monitored actuator 204 power level at the third resonant frequency is below the first threshold power level. The detection module also includes a second threshold power level and outputs a substance 212 not detected signal if the monitored actuator 204 power level at the second resonant frequency is below the second threshold power level. Thus the detection monitor detects a frequency where a monitored actuator 204 power level is near a minimum.

In another example embodiment, the Q-factor of the actuator 204 is tracked as the actuator 204 frequency is scanned to find a frequency of resonance, and hence the speed of sound, for a substance 212 in the cavity 206. During the scan, a frequency having a minimum acoustic resistance identifies the presence or absence of the target substance. See Table in FIG. 5 for an example list of target substances. The frequency having the minimum acoustic resistance node also drains a lesser amount of power from the driver module and thus can be electrically detected.

The substance 212 targeted by the combination sensor 200 can be: a gas, carbon dioxide, a liquid, a solid, a plasma, a molecule, a pathogen, an aerosol, a particulate concentration, pollution and a mixture of the aforementioned substances.

One example application for a non-gas substance is detecting a fine dust air quality. In this example, the compressibility change to the total gas+aerosol can be assumed negligible, so a main difference originates from the density change.

FIG. 1E shows a graph with an estimated speed of sound (c) change as a function of total dust particle mass. One example of an expected dust level: the European air quality standard for fine dust is 25 µgram/m³. According to a calculation, the change in speed of sound is equal to a $CO_2$ concentration change of 35 ppm. This approach can be useful in other applications where there is a much heavier aerosol or particulate loading (e.g. for measuring pollution or smog).

If the substance 212 is a mixture, the speed of sound in the cavity 206 will depend upon an average density of the mixture. Calibration of the combination sensor 200 before use can help identify the target substance 212 within the "noise" floor created by other non-targeted substances.

Figure 4:
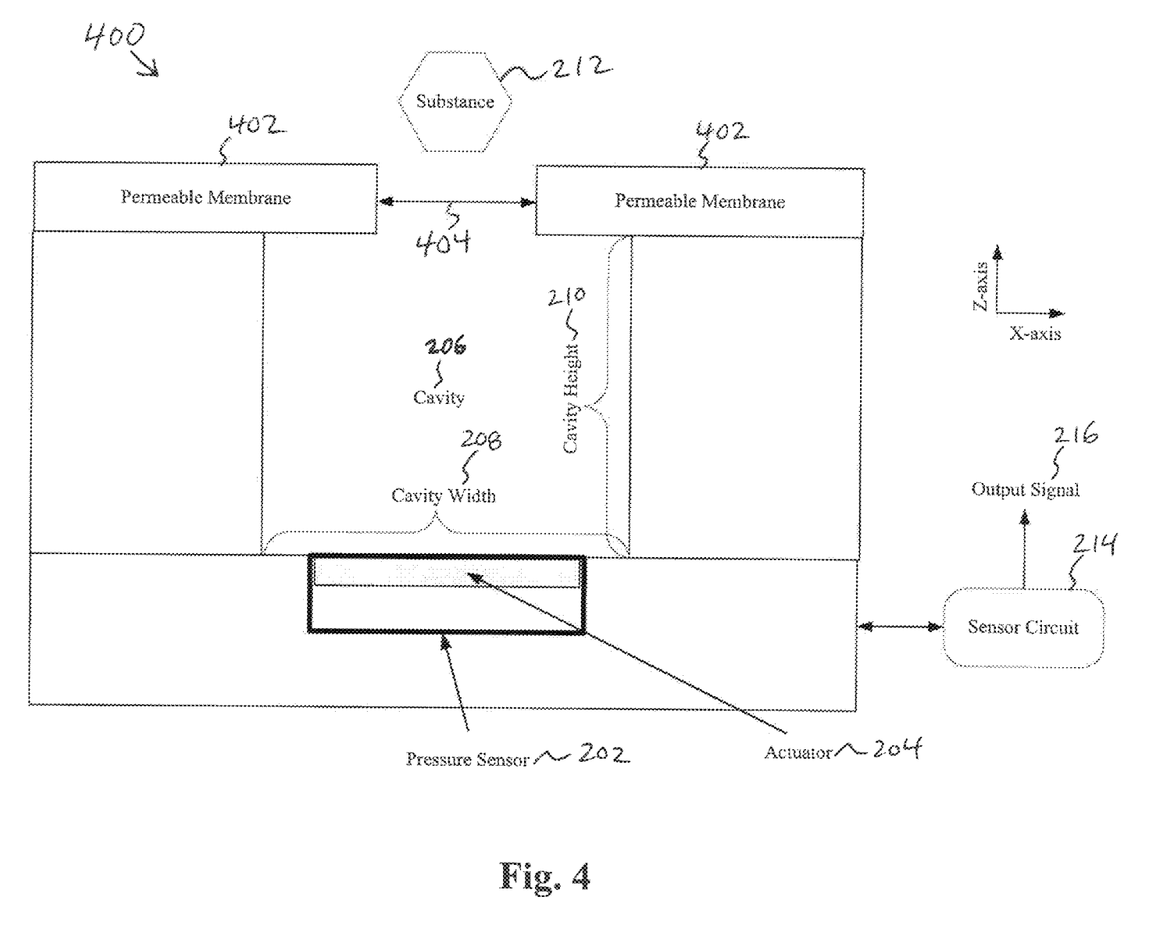
FIG. 4 is one example of a side view of a second combination sensor.

FIG. 4 is one example of a side view of a second combination sensor 400. The example second combination sensor 400 is substantially similar to the first combination sensor 200 but with the addition of a gas-permeable membrane 402 coupled to cover a side of the cavity 206 substantially opposite to the pressure sensor 202.

At least two reasons for adding the gas-permeable membrane 402 include: protecting the cavity 206 and pressure sensor 202; and enabling the combination sensor 400 to be modeled as a closed cavity 206 device.

A closed cavity 206 combination sensor 400 results in a factor of two difference in resonant frequency. As a result, either the width 208, height 210 or length 302 of the cavity 206 can be reduced, or some combination thereof. Such a reduction requires less substrate real-estate and in some examples may lower device fabrication costs. While the size of openings 404 (e.g. degree of permeability, perforations, holes, pores, etc.) will affect the speed of sound calculations, the effects can be empirically accounted for. (e.g. the Table 5 entries can be corrected for the effect).

Should mainly cavity 206 height be a concern, the cavity 206 can also be fabricated as a lateral cavity 206.

Figure 5:
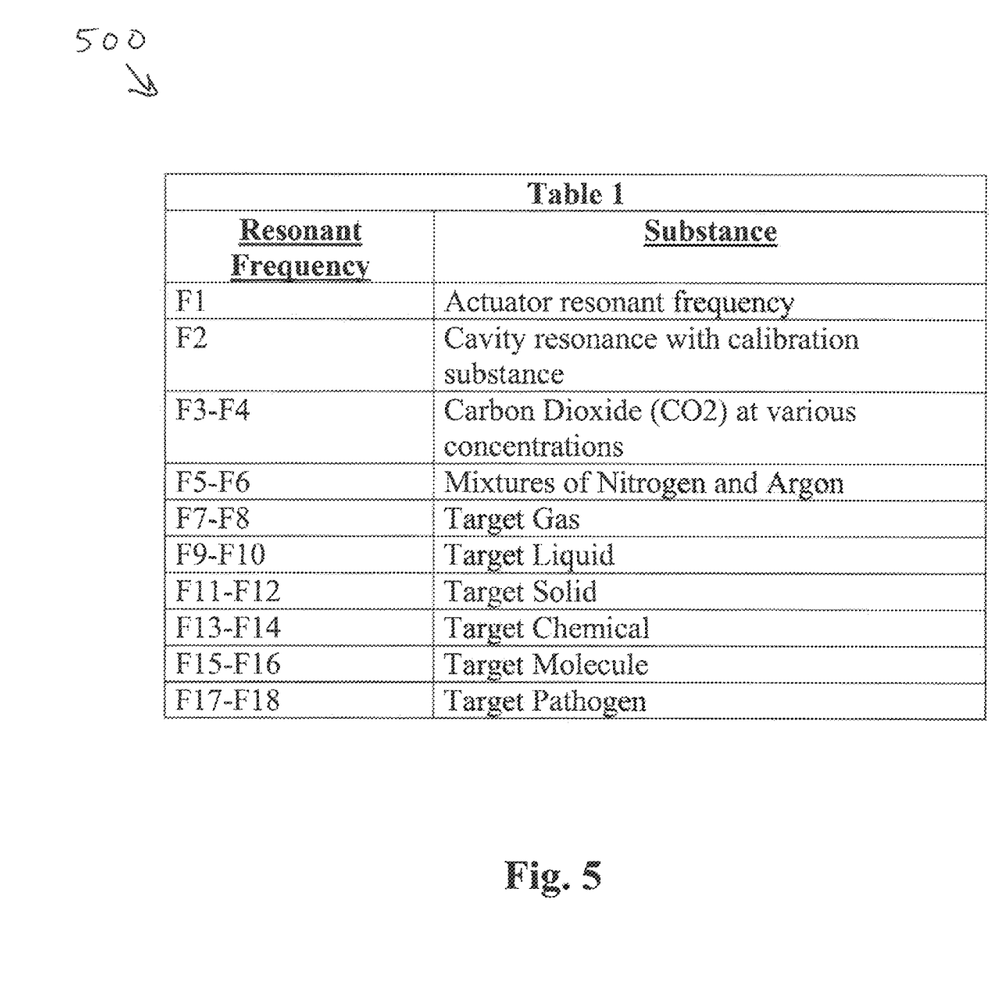
FIG. 5 is one example of a table of substances associated with various resonant frequencies.

FIG. 5 is one example of a table 500 of substances 212 associated with various resonant frequencies. In some example embodiments, the table 500 is stored in the sensor circuit 214. In other example embodiments, the table 500 is stored in a member which is accessible by the sensor circuit 214. Other embodiments of the combination sensor may either not use the table 500 or use a truncated version. Table 500 includes a resonant frequency or range of resonant frequencies. The table 500 matches said resonant frequencies to various substances. For example, resonant frequencies in the range of F3 to F4 are indicative of Carbon Dioxide (CO2) at various molar concentrations. In some example embodiments, more than one combination sensor can be fabricated within a device to monitor multiple ranges of resonant frequencies.

Figure 6:
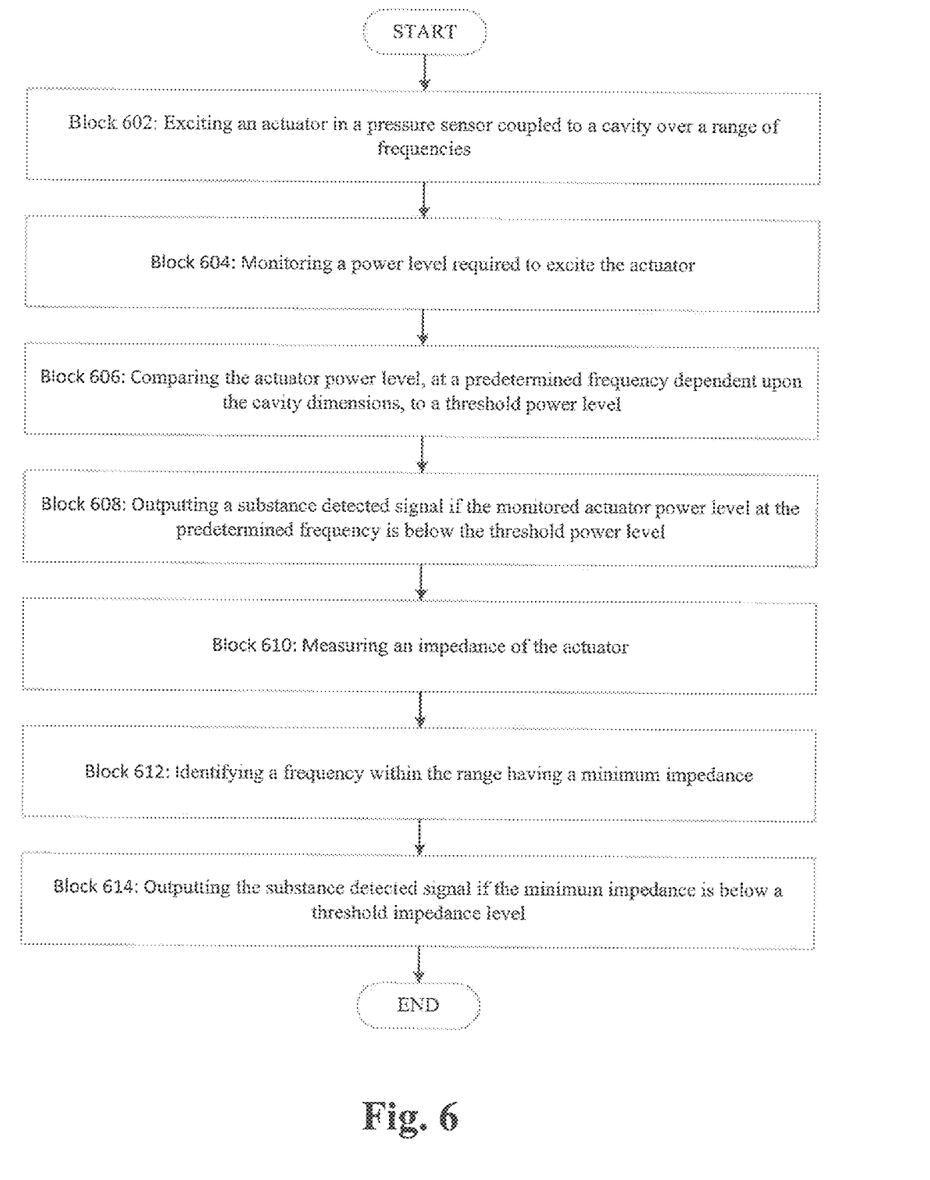
FIG. 6 is one example of a set of instructions for operating a combination sensor.

FIG. 6 is one example of a set of instructions for operating a combination sensor. The set of instructions are presented in one example order of execution. In alternate example embodiments, these instructions can be executed in various other orders.

In block 602, exciting an actuator in a pressure sensor coupled to a cavity over a range of frequencies. Next, in block 604, monitoring a power level required to excite the actuator. In block 606, comparing the actuator power level, at a predetermined frequency dependent upon the cavity dimensions, to a threshold power level. Then in block 608, outputting a substance detected signal if the monitored actuator power level at the predetermined frequency is below the threshold power level.

These instructions can be augmented with one or more of the following instructions, presented in no particular order.

In block 610, measuring an impedance of the actuator. In block 612, identifying a frequency within the range having a minimum impedance. In block 614, outputting the substance detected signal if the minimum impedance is below a threshold impedance level.

Figure 7:
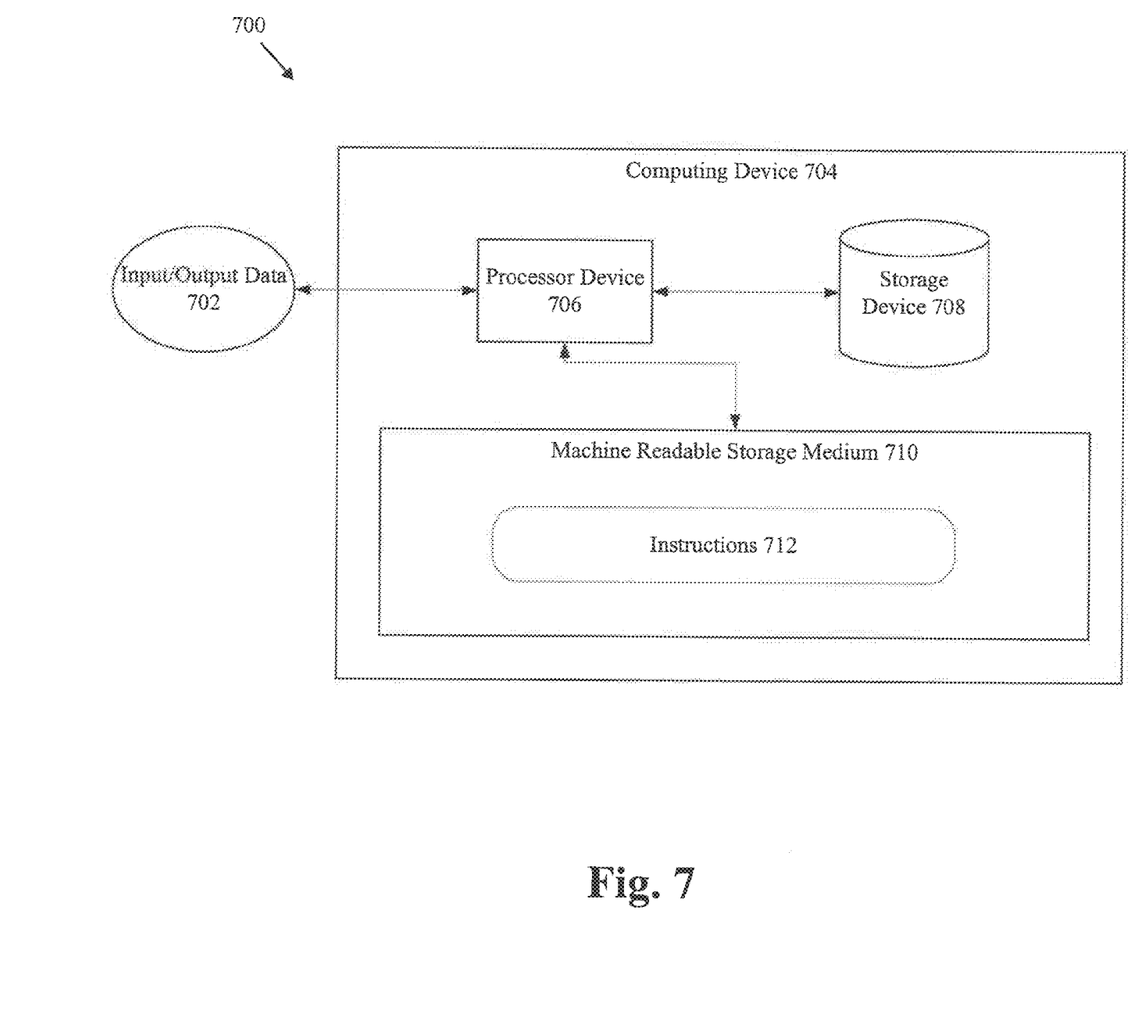
FIG. 7 is one example of a sensor circuit for operating a combination sensor.

FIG. 7 is one example of a sensor circuit 108 for operating a combination sensor 200. The sensor circuit 108 includes an input/output data 702 interface with an electronic apparatus 704. The electronic apparatus 704 includes a processor 706, a storage device 708, and a machine-readable storage medium 710. The machine-readable storage medium 710 includes instructions 712 which control how the processor 706 receives input data 702 and transforms the input data into output data 702, using data within the storage device 708. Example instructions 712 stored in the machine-readable storage medium 710 are discussed with respect to FIG. 5 above. The machine-readable storage medium in an alternate example embodiment is a computer-readable storage medium.

The processor (such as a central processing unit, CPU, microprocessor, application-specific integrated circuit (ASIC), etc.) controls the overall operation of the storage device (such as random access memory (RAM) for temporary data storage, read only memory (ROM) for permanent data storage, firmware, flash memory, external and internal hard-disk drives, and the like). The processor device communicates with the storage device and machine-readable storage medium using a bus and performs operations and tasks that implement one or more blocks stored in the machine-readable storage medium. The machine-readable storage medium in an alternate example embodiment is a computer-readable storage medium.

The blocks comprising the flowcharts in the above Figures can be executed in any order, unless a specific order is explicitly stated. Also, those skilled in the art will recognize that while one example method embodiment is now discussed, the material in this specification can be combined in a variety of ways to yield other examples as well. The method next discussed is to be understood within a context provided by this and other portions of this detailed description.

In this specification, example embodiments have been presented in terms of a selected set of details. However, a person of ordinary skill in the art would understand that many other example embodiments may be practiced which include a different selected set of these details. It is intended that the following claims cover all possible example embodiments.

What is claimed is:

1. A combination sensor, comprising:
   a pressure sensor having an actuator which has a first resonant frequency;
   a cavity, coupled to the pressure sensor and able to receive a substance;
   wherein the cavity, in an absence of the substance, has a second resonant frequency in response to excitation by the actuator;
   wherein the cavity, in a presence of the substance, has a third resonant frequency in response to excitation by the actuator;
   wherein the first resonant frequency differs from the second and third resonant frequencies;
   a sensor circuit including a driver module configured to excite the actuator, an actuator power level monitor and a detection module,
   wherein the detection module is configured to output a substance detected signal in response to the third resonant frequency in the cavity;
   wherein the sensor circuit is embedded within a semiconductor chip covered by an overmolding layer, wherein the cavity is an opening within the overmolding layer, wherein the opening has a width, a height, and a length, and
   wherein the first, second and third cavity resonant frequencies are based on the width, height and length of the overmolding layer opening.

2. The combination sensor of claim 1:
   wherein the first resonant frequency is higher than the second and third resonant frequencies.

3. The combination sensor of claim 1:
   wherein the second and third resonant frequencies depend upon a speed of sound in the substance.

4. The combination sensor of claim 1:
   wherein the cavity includes a physical dimension such that the third resonant frequency indicates presence of a target substance.

5. The combination sensor of claim 1:
   wherein the substance is at least one from a group consisting of: a gas, carbon dioxide, a liquid, a solid, a plasma, a molecule, a pathogen, an aerosol, a particulate concentration, pollution and a mixture of the aforementioned substances.

6. The combination sensor of claim 1:
   wherein a pressure wave in the cavity can be created in response to power from the sensor circuit.

7. The combination sensor of claim 1:
   wherein the sensor circuit includes an actuator power level monitor and a detection module;
   wherein the detection module includes a first threshold power level and outputs the substance detected signal if a monitored actuator power level at the third resonant frequency is below the first threshold power level.

8. The combination sensor of claim 7:
   wherein the detection module includes a second threshold power level and outputs a substance not detected signal if the monitored actuator power level at the second resonant frequency is below the second threshold power level.

9. The combination sensor of claim 1:
   wherein the sensor circuit includes an actuator power level monitor, a detection module and a driver module;
   wherein the driver module includes a frequency generator which excites the actuator and includes a circuit capable of varying the excitation frequency of the actuator over a range of frequencies; and
   wherein the detection module includes a circuit for detecting a frequency where a monitored actuator power level is near a minimum.

10. The combination sensor of claim 1:
    wherein the sensor circuit includes a frequency generator;
    wherein the frequency generator excites the actuator; and
    wherein the frequency generator does not excite the actuator while the sensor circuit is using the pressure sensor to monitor a pressure in the cavity.

11. The combination sensor of claim 1:
    wherein the combination sensor is formed at least in part from at least one from a group consisting of: bulk wafer material, wafer surface material deposition, overmolding, packaging, a MEMS device and a CMOS device.

12. The combination sensor of claim 1:
wherein the pressure sensor includes a capacitive pressure sensor membrane; and
wherein the actuator is the capacitive pressure sensor membrane.

13. The combination sensor of claim 1:
further comprising a gas-permeable membrane coupled to cover a side of the cavity substantially opposite to the pressure sensor.

14. The combination sensor of claim 1:
wherein the combination sensor is part of at least one from a group consisting of: a CO2 monitoring system, an indoor monitoring system, a food quality monitoring system, an air quality control system, and a mobile device.

15. A combination gas pressure sensor and carbon dioxide level sensor, comprising:
a cavity, coupled to the pressure sensor and coupled to expose the cavity and the pressure sensor to a gas;
wherein the gas pressure sensor includes a membrane;
wherein the cavity has a predetermined resonant frequency in response to excitation by the membrane when carbon dioxide is in the cavity;
a sensor circuit including a driver module configured to excite the membrane, a membrane power level monitor and a detection module,
wherein the detection module is configured to output a carbon dioxide detected signal in response to the predetermined resonant frequency in the cavity,
wherein the sensor circuit is embedded within a semiconductor chip covered by an overmolding layer,
wherein the cavity is an opening within the overmolding layer,
wherein the opening has a width, a height, and a length, and
wherein the predetermined resonant frequency is based on the width, height and length of the overmolding layer opening.

16. An article of manufacture comprising at least one non-transitory, tangible machine readable storage medium containing executable machine instructions for operating a combination sensor, the instructions comprising:
exciting an actuator in a pressure sensor coupled to a cavity over a range of frequencies;
monitoring a power level required to excite the actuator;
comparing the actuator power level, at a predetermined frequency dependent upon the cavity dimensions, to a threshold power level; and
outputting a substance detected signal if the monitored actuator power level at the predetermined frequency is below the threshold power level;
wherein the combination sensor includes a sensor circuit having a driver module configured to excite the actuator, an actuator power level monitor and a detection module;
wherein the detection module is configured to output the substance detected signal;
wherein the sensor circuit is embedded within a semiconductor chip covered by an overmolding layer,
wherein the cavity is an opening within the overmolding layer,
wherein the opening has a width, a height, and a length and defines the cavity dimensions, and
wherein the predetermined frequency is based on the width, height and length of the overmolding layer opening.

17. The instructions of claim 16:
wherein monitoring includes:
measuring an impedance of the actuator; and
identifying a frequency within the range having a minimum impedance; and
wherein outputting includes outputting the substance detected signal if the minimum impedance is below a threshold impedance level.

18. The instructions of claim 16:
wherein the substance is a mixture containing carbon dioxide gas.

19. The instructions of claim 16:
wherein the monitored actuator power level is below the threshold power level at a resonant frequency of the cavity.

* * * * *